US00RE34740E

United States Patent [19]

Kawabata et al.

[11] E Patent Number: Re. 34,740

[45] Reissued Date of Patent: Sep. 27, 1994

[54] ADSORPTIVE RESIN FOR MICROORGANISMS

[75] Inventors: Nariyoshi Kawabata, Osaka; Akinori Minami; Tadahira Yo, both of Ibaragi, all of Japan

[73] Assignee: Japane Vilkene Company, Ltd., Tokyo, Japan

[21] Appl. No.: 163,327

[22] Filed: Dec. 6, 1993

Related U.S. Patent Documents

Reissue of:

[64] Patent No.: 5,185,415
Issued: Feb. 9, 1993
Appl. No.: 809,208
Filed: Dec. 13, 1991

U.S. Applications:

[63] Continuation of Ser. No. 550,967, Jul. 11, 1990, abandoned.

[30] Foreign Application Priority Data

Jul. 12, 1989 [JP] Japan ..... 1-181576

[51] Int. Cl.[5] ..... C08F 26/06

[52] U.S. Cl. ..... 526/265; 210/616; 525/279; 526/253; 526/317.1; 526/319; 526/347; 526/348.8

[58] Field of Search ..... 526/265, 253; 525/279

[56] References Cited

U.S. PATENT DOCUMENTS

| | | | |
|---|---|---|---|
| 3,901,804 | 8/1975 | Ohuchi | 210/711 |
| 4,060,456 | 11/1977 | Long | 435/94 |
| 4,222,881 | 9/1980 | Byham | 526/265 |
| 4,808,412 | 2/1989 | Smith | 424/442 |
| 4,832,984 | 5/1989 | Hasegawa | 427/161 |
| 4,913,820 | 4/1990 | Kawabata | 210/616 |

FOREIGN PATENT DOCUMENTS

| | | |
|---|---|---|
| 58-154502 | 9/1983 | Japan . |
| 153998 | 8/1985 | Japan . |

*Primary Examiner*—Fred Zitomer
*Attorney, Agent, or Firm*—Lorusso & Loud

[57] ABSTRACT

The present invention relates to absorption resins comprising vinyl copolymers which do not dissolve in water and are capable of absorbing microorganisms without inactivating the microorganisms and also adsorbents with a large contact area which are capable of absorbing microorganisms efficiently as well as methods of making the resins and the adsorbents.

13 Claims, No Drawings

ADSORPTIVE RESIN FOR MICROORGANISMS

Matter enclosed in heavy brackets [ ] appears in the original patent but forms no part of this reissue specification; matter printed in italics indicates the additions made by reissue.

This is a continuation of copending application Ser. No. 07/550,967 filed on Jul. 11, 1990 now abandoned.

DETAILED EXPLANATION OF THE INVENTION

1. Industrial Field of Application

The present invention relates to absorptive resins which do not dissolve in water and are capable of adsorbing microorganisms without inactivating the microorganisms and also adsorbents with a large contact area which are capable of adsorbing microorganisms efficiently as well as methods of making the resins and the adsorbents.

2. Prior Art

It has previously been proposed to provide means to adsorb microorganisms in service water or in sewage by using water soluble chemical substances such as chlorine which posses a germicidal power. However, those chemical substances, in general, are often toxic and therefore unsuitable for use in drinking water or water for production of foods as well as medicines. Chlorine, for instance, produces organic halogens such as trihalomethane during water treatment. Trihalomethane was recently found to be carcinogenic and also subject to biological concentrations, a rising problem of environmental protection movements.

There has long been a need for a new substance which is water insoluble and able to remove microorganisms.

In the field of bioreactors and biosensors, enzyme produced by microorganisms which are fixed to carriers live are being considered. Some methods such as physical adsorption and covalent bonding are presently known to be capable to fix microorganisms to carriers. The physical adsorption provides weak cohesion and microorganisms may drift away. On the other hand, the covalent bonding provides relatively strong cohesion, but enzyme may denature in reaction or die out. The demands for a carrier which is capable of stably fixing microorganisms without exterminating or inactivating microorganisms have been strong.

Japanese patent publication No. 41641/87 proposes insoluble high polymers comprising cross-linked polyvinyl pyridinium halide as a material to satisfy the demands for a remover of microorganisms in water treatment as well as for a carrier in a bioreactor.

This chemical compound, insoluble in water as well as capable of efficiently adsorbing and retaining microorganisms live, makes an excellent adsorbent of microorganisms and does not contaminate the environment.

Said cross-linked polyvinyl pyridinium halide, however, is insoluble not only in water but also in an ordinary organic solvent. A number of problems such as working on the chemical is difficult for it is usually used only in a solid state arise as beads and the surface area per unit weight is small, decreasing adsorption of microorganisms. In order to increase surface area, the size of beads, for example, could be made smaller, however, such tiny beads might cause clogging of the system.

In view of the present situation described above, the present invention is to overcome the problems of known adsorptive resins that are insoluble not only in water but also in a organic solvent difficult to working with and poor adsorptive performance for the weight.

Accordingly it is an object of the present invention to provide adsorptive resins which are insoluble or hard to dissolve in water but soluble in an organic solvent, easy to work on, capable of efficiently adsorbing microorganisms by having a large surface area per unit weight and which do not inactivate the microorganisms and also to provide adsorbents which comprise the adsorptive resins, as well as methods to make the adsorptive resins and the adsorbents.

SUMMARY OF THE INVENTION

An adsorptive resin of the present invention comprises vinyl copolymers of the formula

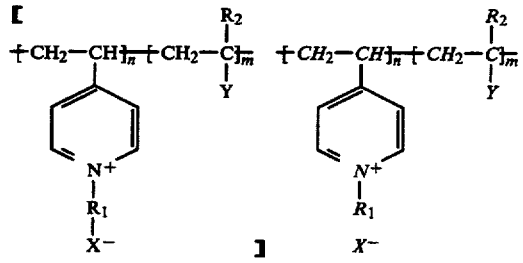

wherein $R^1$ is a benzyl group, an alkyl group of 4 to 16 carbon atoms or a pentafluorophenylmethyl group, $R^2$ is a hydrogen atom or an alkyl group of 1 to 3 carbon atoms, X is a halogen atom, and Y is a hydrogen atom, an alkyl group of 1 to 3 carbon atoms, a benzyl group, and ether group, a carboxyl group, a carboxylic acid ester group or an aryl group.

An adsorptive resin of the present invention possesses an adsorptive power comparable to cross-linked polyvinyl pyridinium halide, and is insoluble or hard to dissolve in water but soluble in an organic solvent as well as capable of making an organic solution. Accordingly impregnation of the adsorptive resin into or coating it onto a base material has become possible, which was impossible with the known cross-linked polyvinyl pyridinium halide.

DETAILED DESCRIPTION OF THE INVENTION

An adsorptive resin of the present invention comprises vinyl copolymers of the formula,

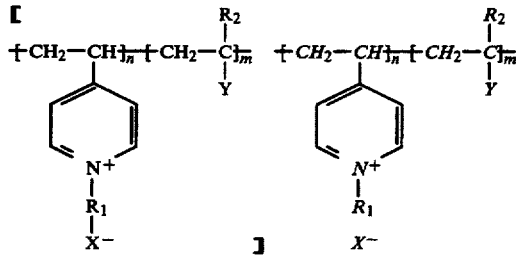

wherein $R^1$ is a benzyl group, an alkyl group of 4 to 16 carbon atoms or a pentafluorophenylmethyl group, $R^2$ is a hydrogen atom or an alkyl group of 1 to 3 carbon atoms, X is a halogen atom, and Y is a hydrogen atom, an alkyl group of 1 to 3 carbon atoms, a benzyl group, an ether group, a carboxyl group, a carboxylic acid ester group or an aryl group, which are obtained after copolymerizing 4-vinyl pyridine and monovinyl monomer, and acting halide, said vinyl copolymers being random copolymers or block copolymers.

Monovinyl monomers to be used for copolymerization are olefine such as ethylene, propylene and butylen and the like, styrene, vinyl acetate, acrylic acid, acrylic acid ester, methacrylic acid, methacrylic acid ester, aliphatic vinyl ester, acrylnitrile and their derivatives. Others may also be used alone or in combination. However, monovinyl monomers that posses a highly hydrophilic functional group should be avoided, for some copolymers obtained using such hydrophilic functional group may become water soluble.

The ratio of 4-vinyl pyridine and monovinyl monomer (n:m) differs according to the kinds or copolymerizational degrees. It is recommended that n:m be within an approximate range of 10:90 to 90:10. If the proportion of 4-vinyl pyridine is below the range, a sufficient adsorptive power cannot be gained and if it exceeds the range, the resulting copolymers become highly water soluble.

The copolymerizational degree of said vinyl copolymers should be at least 300. If less than that degree, the obtained copolymers become highly water soluble.

The copolymers of 4-vinyl pyridine and monovinyl monomer form a functional group of the formula, $$[X^{-}—R_1—N^{-}]$$

$$X^{-}R_1—N$$

by quaternizing pyridin with halide such as alkyl halide, benzyl halide and pentafluorophenylmethyl halide.

This functional group is considered to be a significant in adsorbing microorganisms and retaining the microorganisms in an active state. The mechanism of it is not yet clear, however, it is estimated that an electrostatical interaction is a key factor for the mechanism. That is, the electrically plus charged functional group attracts microorganisms the surface of whose cell is generally minus charged.

The term "microorganisms" is used herein to mean bacteria, fungi, algae, viruses and the like.

An excellent remover of microorganisms for water treatment and an excellent adsorbent of microorganisms for use as a carrier in a bioreactor or a biosensor can be obtained by firmly adhering to the surface of a base material an adsorptive resin comprising vinyl copolymers in the adhering steps as described below.

An adsorptive resin of microorganisms produced in the process described in the above is soluble in an organic solvent but insoluble or hardly soluble in water.

An adsorbent of microorganisms is obtained by:

dissolving an adsorptive resin of the present invention in an organic solvent such as alcohol, ester and ether, making a non-water solution;

adhering the non-water solution on a base material by impregnating, spraying or coating; and drying the base material so as to firmly adhere the adsorptive resin to the surface of the base material.

From a standpoint of easy handling, a desirable organic solvent is alcohol. And, a desirable way to adhere an adsorptive resin to a base material as widely inside and evenly as possible is impregnation.

There exists no particular limitation to the amount of said adsorptive resin of microorganisms to be used on a base material, however, it provides a peak adsorption and cost performance in the range between 0.001 and 1 μm in thickness of adhered adsorptive resin, which means roughly 0.001 to 100 wt % of a base material. When it is less than 0.001 wt %, a sufficient enough adsorptive power cannot be expected and when it exceeds 100 wt , an increase of the amount of an adsorptive resin does not proportionally result in an increase of the adsorptive power. When a nonwoven fabric is used as a base material, the range of 0.01 to 20 wt % provides a high adsorption and fine cost performance.

A variety of materials such as a porous material like a nonwoven fabric, a woven fabric, knitted goods, paper, foamy materials and a ceramic sinter, organic or inorganic beads, or a honeycomb or a multistage board can be used as a base material for the adsorbent of microorganisms, and it is possible to select from among either single or compound, organic, inorganic or metal substances. Among these, porous materials are best recommended as they have a large surface area. And among porous materials, a nonwoven fabric is better selected for it is three-dimensional, gives a large surface area and is able to lower pressure loss. In addition, an adsorptive resin evenly and thinly adheres to the surface of fibers that constitute a nonwoven fabric, the surface area per weight of an adsorptive resin becoming much larger than that in the case of beads. It is then possible to sharply increase the surface area of a nonwoven base material that contacts microorganisms in water treatment and accordingly the efficiency of reaction in a bioreactor. It is also possible, by controlling the density of a nonwoven fabric, to give the nonwoven base material a structure which is hard to clog when a large quantity of microorganisms is adsorbed.

When an adsorbent of microorganisms is used in water treatment, water is purified by removal of microorganisms in the water by the adsorbent. When it is used for a bioreactor either in an atmosphere or in a liquid, it adsorbs microorganisms possessing specific functions in a living and a highly active state, and some products can be obtained by activating enzyme in the microorganisms, or substances can be sorted.

Further, when an adsorbent of microorganisms is used for an airfilter or a mask, viruses and bacteria can be collected together with other harmful substances and dusts in the air.

It is also possible to adhere an adsorptive resin of the present invention to the surface of a base material together with a germicide.

The term "germicide" as used herein includes a germicide that sterilizes microorganisms and a germicide that prevents microorganisms from propagating or holds microorganisms under control. Suitable germicides are antibiotics such as polymixin, positive surfactants such as quaternary ammonium salt, ampholytic surfactants such as alkylaminoethylglycine, biguanides such as chlorhexidine and polyhexamethylene biguanide, higher fatty acids such as undecylenic acid, metal or metal ion and phenol.

These germicides can be adhered to the surface of a base material together with an adsorptive resin of the present invention by impregnating, spraying or coating. Also, when a base material composing a porous material such as a nonwoven fabric is used, these germicides can be placed in the base material in the form of germicidal fibers or resistive fibers that contain a germicide.

Germicides used for an absorbent of microorganisms in an atmosphere can be any of those above, however, when the adsorbent is used in water, especially in treatment of drinking water, it is harmful if germicides are dissolved in the water. In order to avoid the problem, germicides to be used in water should be insoluble or hardly soluble in water. Recommendable germicides are metal powders such as gold, silver or copper powders, antibacterial zeolite made by permuting zeolite with germicidal metal ions, polymer- type fixed germicides made by fixing biguanide or quaternary ammonium salt to polymers such as polyvinyl, polyacrylate, polyester and polyamide or silicon-type fixed germicides such as 3-(trimetoxysilil)-propyltrimethyloctadecil ammoniumchrolide.

The adhesion process of said germicides to a base material can be performed at any point of the procedure. It can be performed before adhering an adsorptive resin of microorganisms of the present invention to the base material, after, or simultaneous with the adhesion of the resin. The method of adhering a germicide to a base material may be directly adhering a germicide to a base material or impregnating, spraying or coating an organic solvent solution in which a germicide is dissolved or scattered, then blowing away the organic solvent. Especially when a germicide is to be adhered together with an adsorptive resin of the present invention to a base material, it is recommended that the germicide be dissolved or scattered in an organic solvent solution of the adsorptive resin.

In order to adhere a germicide in a base material, the germicide is contained in the component of a base material such as a fiber, a porous material, or a film and a resin sheet or a germicidal functional group is induced into the component.

The amount of a germicide will depend on the kind and the germicidal power of the germicide, however, the amount should be enough to prevent collected microorganisms from propergating.

An adsorbent of the present invention is capable of adsorbing microorganisms in water or in the air very effectively, and either sterilizes the microorganisms with a germicide or prevents them from propagating.

According to the research reports made by the inventors and other researchers of the present invention, it is clear that the adsorptive capability of an adsorbent of microorganisms of the present invention is excellent in water but not very satisfactory in the air. Therefore, when an adsorbent of microorganisms is to be used in an atmosphere, it is desired that the atmosphere is a highly moist gas or a moistener exists on the surface of the base material together with an adsorptive resin of the present invention. It is better to utilize a humidifying means such as a humidifier to humidify the atmosphere.

Moisteners to be used for said adsorbents of microorganisms of the present invention can be any that adsorbs moisture in an atmosphere, for example, alkali earth metallic salts such as calcium chloride and magnesium chloride, deliquescent substances such as lithium chloride, potassium metasolicic acid and titanium sulfate, water soluble polymers such as polyvinyl alcohol, polyacrylate, polyvinyl pyrrolidone and carboxymethylcellulose, silica gel, zeolite, collagen, ethylene glycol, diphosphoric pentoxide, magnesium oxide or calcium oxide.

These moisteners can be adhered to the surface of the base material together with said adsorptive resin by impregnating, spraying or coating.

Adhesion of a moistener is to be conducted before or after adhesion of an adsorptive resin consisting of said vinyl copolymers, or conducted simultaneously. Especially when adhesion of a moistener is conducted simultaneously with adhesion of an adsorptive resin a moistener is to be put in an organic solvent solution of said adsorptive resin of microorganisms to coexist. If a moistener is soluble in an organic solvent, it dissolves in the solution together with an adsorptive resin, and if it is not soluble, it is scattered in the solution.

The amount of a moistener is recommended to be approximately 5–500 wt % of the amount of an adsorptive resin to be used though, the amount depends on the kind of a moistener and the adsorptive power of moisture. When the amount is less than the range, it cannot supply enough moisture to keep active the adsorptive part of an adsorptive resin of the present invention, and when the amount is in excess of the range, the adsorptive power of moisture does not improve in proportion to the increase the amount of the moistener.

An adsorbent of microorganisms using said adsorptive resin of microorganisms can be used for a mask or an airfilter. In these cases, an adsorbent may be used without modification, or may be used with a germicide and a moistener on the surface of a base material together with an adsorptive resin of the present invention. In order to adhere a germicide together with a moistener, a germicide is to be adhered to the surface of a base material or a germicidal fiber containing a germicide or a germicidal fiber to which a functional group is induced is to be used as a component of a base material. When a germicide is used together with an adsorptive resin of the present invention, the adhered microorganisms become unable to propagate, which prevents clogging of the system and elongates the life of a mask and an airfilter.

WORKING EXAMPLES

Adsorptive resins and adsorbents of microorganisms of the present invention, and the methods of making them are described in detail in the following, with the help of working examples.

4-vinyl pyridine, stylene and methyl methacrylate monomer for the following working examples are all obtainable by refining chemicals on the market by a process such as decompression distillation.

WORKING EXAMPLE 1

An adsorptive resin comprising vinyl copolymers was obtained in the steps:

- putting in a reactor 0.84 g (5 m mol) of 2,2'-azobisisobutyronitrile (purity 98%) and 533.84 g of ethanol (purity 99%) and regulating a catalytic solution;
- putting in 4-vinylpyridine (105.14 g, 1,000 m mol) and stylene (156.23 g, 1,500 m mol) in the proportion of 1:1.5 mol; and
- copolymerizing them in an nitrogen atmosphere for six hours at 78° C.; and then
- putting in 174.53 g (1,000 m mol) of benzylbromide (purity 98%) and quaternizing them for six hours at 78° C.

Table 1 shows the description above in figures.

For the convenience of easy understanding and easy calculation, the amount of 4-vinyl pyridine is uniformly made one mol.

TABLE 1

| chemical compound | 4-vinyl pyridine | stylene | benzyl bromide | 2,2'-azobisiso-buty-ronitrile | ethyl alcohol |
|---|---|---|---|---|---|
| abbreviation | 4VP | ST | BzBr | AIBN | EtOH |
| ratio of monomer | 1 | 1.5 | | | |
| mol % (monomer = 100) | 40 | 60 | 40 | 0.2 | |
| molecular weight (g/mol) | 105.14 | 104.15 | 171.04 | 164.21 | 46.07 |
| purity (%) | 100 | 100 | 98 | 98 | 99 |
| calculative annexing (m mol) | 1,000 | 1,500 | 1,000 | 5 | |
| annexing amount (g) | 105.14 | 156.23 | 174.53 | 0.84 | *533.84 |

*In order to make monomer concentration 45 wt % the necessary EtOH = {[(105.14 − 156.23 − 171.04)/0.45] − (105.14 − 156.23 − 171.04)}/0.99 = 533.84

On the other hand, a fiber web made of rayon fiber (1.5 deniers) was made into a nonwoven fabric of 90 g/m$^2$ and 0.5 mm thick by water entanglement.

After impregnating an 0.5 wt % ethanol solution in which said vinyl copolymers were dissolved into said nonwoven fabric, the nonwoven fabric was dried at 75° C. and an adsorbent of microorganisms of which 1.5 wt % was copolymers was obtained.

Stamping out discs whose diameter was 3 cm from the adsorbent, and filling 30 discs in a column whose inside diameter was 3 cm. a suspension with *Escherichia coli* concentration of $46\times10^8$/ml in 0.85% salt water was sent through the column at a velocity of 45 ml/hr.

Table 3 shows the results of removal rates of living microorganisms in the filtrate, which was taken at regular intervals of time by the agar plate culture method.

COMPARISON EXAMPLE 1

Another nonwoven fabric was made in the same process of Working Example 1, except that no adsorptive resin was used, and 30 discs were filled in another column in the same manner, and a suspension with an *Escherichia coli* concentration of $5.5\times10^8$/ml in 0.85% salt water was sent through the column at a velocity of 35 ml/hr.

Table 3 shows the results of removal rate of living microorganism in the filtrate, which was taken at regular intervals of time by the agar plate culture method.

WORKING EXAMPLE 2

An adsorptive resin was obtained as described in Working Example 1, except that the amount of ethanol was changed to 47.96 g, and 127.87 g (1,000 m mol) of benzyl chloride (purity 99%) was used instead of benzyl bromide.

Table 2 shows the description above in figures.

For the convenience of easy understanding and easy calculation, the amount of 4-vinyl pyridine is uniformly made one mol.

Discs taken from the absorbent made in the same process of Working Example 1 were filled in still another column in the same manner as in Working Example 1 and a suspension with *Escherichia coli* concentration of $5.6\times10^8$/ml in 0.85% salt water was sent through the column at a velocity of 40 ml/hr.

Table 3 shows the results of removal rate of living microorganisms in the filtrate, which was taken at regular intervals of time by the agar culture method.

As is apparent from Table 3, the adsorbents of microorganisms of Working Examples 1 and 2, to both of which vinyl copolymers were adhered, shows an excellent adsorption of microorganisms and a high removal rate of microorganisms, while the adsorbent without vinyl copolymers in Comparison Example 1 shows poor adsorption, which went poorer with time, the removal rate of microorganism becoming mere 10% or so in 2 hours.

TABLE 1

| chemical compound | 4-vinyl pyridine | stylene | benzyl bromide | 2,2'-azobisiso-buty-ronitrile | ethyl alcohol |
|---|---|---|---|---|---|
| abbreviation | 4VP | ST | BzCl | AIBN | EtOH |
| ratio of monomer | 1 | 1.5 | | | |
| mol % (monomer = 100) | 40 | 60 | 40 | 0.2 | |
| molecular weight (g/mol) | 105.14 | 104.15 | 126.59 | 164.21 | 46.07 |
| purity (%) | 100 | 100 | 98 | 98 | 99 |
| calculative annexing (m mol) | 1,000 | 1,500 | 1,000 | 5 | |
| annexing amount (g) | 105.14 | 156.23 | 127.87 | 0.84 | 478.96 |

TABLE 3

| | Working Example 1 | Working Example 2 | Comparison Example 1 |
|---|---|---|---|
| vinyl copolymers | existent | existent | none |
| quaternizing component | benzyl bromide | benzyl chloride | |
| microorganisms in water (No./ml) | $4.6\times10^8$ | $5.6\times10^8$ | $5.5\times10^8$ |
| microorganisms in filtrated water 1 hr. later (No./ml) | $1.4\times10^4$ | $4.6\times10^4$ | $3.1\times10^8$ |
| rate of removal (%) | 99.997 | 99.992 | 43.6 |
| microorganism in filtrated water 2 hrs. later (No./ml) | $3.7\times10^5$ | $5.5\times10^5$ | $4.9\times10^8$ |
| rate of removal (%) | 99.92 | 99.90 | 10.9 |

WORKING EXAMPLE 3

Discs taken from yet another adsorbent made in the same process of Working Example 1 were filled in yet another column in the same manner as in Working Example 1, and a suspension with Staphylococcus aureus; concentration of $2.8\times10^8$/ml in 0.85% salt water was sent through the column at a velocity of 60 ml/hr.

Table 4 shows the results of removal rate of living microorganisms in the filtrate, which was taken at regular intervals of time.

WORKING EXAMPLE 4

Discs taken from yet still another adsorbent made in the same process of Working Example 1 were filled in yet still another column in the same manner as in Working Example 1, and a suspension with *Pseudomonas aeruginosa* concentration of $6.2\times10^8$/ml in 0.85% salt water was sent through the column at a velocity of 30 ml/hr.

Table 4 shows the results of removal rate of living microorganism in the filtrate, which was taken at regular intervals of time.

As is apparent from Table 4, adsorbents of microorganisms with the use of an adsorptive resin of the present invention showed an excellent adsorption disregarding types of microorganisms.

TABLE 4

| | Working Example 1 | Working Example 3 | Working Example 4 |
|---|---|---|---|
| type of microorganism | *Escherichia coli* | *staphylococcus Aureus* | *Pseudomonas Aeruginosa* |
| microorganism in water (No./ml) | $4.6 \times 10^8$ | $2.8 \times 10^8$ | $6.2 \times 10^8$ |
| microorganism in filtrated water 1 hr. later (No./ml) | $1.4 \times 10^4$ | $9.2 \times 10^3$ | $8.2 \times 10^4$ |
| rate of removal (%) | 99.997 | 99.990 | 99.990 |
| microorganism in filtrated water 2 hrs. later (No./ml) | $3.7 \times 10^5$ | $5.2 \times 10^5$ | $2.2 \times 10^8$ |
| rate of removal (%) | 99.92 | 99.81 | 99.64 |

WORKING EXAMPLE 5

Twenty discs with a diameter of 1.6 cm taken from another adsorbent made in the same process of Working Example 1 were filled in another column with an inside diameter of 1.6 cm in the same manner as in Working Example 1, and a suspension with T-4 bacteriophage concentration of $1.3 \times 10^6$/ml in 0.85% salt water was sent through the column at a velocity of 20 ml/hr.

Table 5 shows the results of removal rate of living microorganisms in the filtrate, which was taken at regular intervals of time.

COMPARISON EXAMPLE 2

Without using an adsorptive resin of the present invention, a nonwoven fabric was filled in a column, and a suspension with T-4 bacteriophage concentration of $1.3 \times 10^6$/ml in 0.85% salt water was sent through the column at a velocity of 20 ml/hr.

Table 5 shows the results of removal rate of living microorganisms in the filtrate, which was taken at regular intervals of time.

Table 5 also shows that an absorbent with the use of an adsorptive resin works effectively on viruses which are tinier than fungi.

TABLE 5

| | Working Example 5 | Comparison Example 2 |
|---|---|---|
| vinyl copolymers | existent | none |
| type of microorganisms | T-4 *bacteriophage* | T-4 *bacteriophage* |
| microorganisms in water (No./ml) | $1.3 \times 10^6$ | $1.3 \times 10^6$ |
| microorganism in filtrated water 1 hr. later (No./ml) | $2.3 \times 10^2$ | $4.6 \times 10^5$ |
| rate of removal (%) | 99.98 | 65.0 |

WORKING EXAMPLE 6

An adsorbent of microorganisms was obtained as described in Working Example 1, except that the ratio of 4-vinyl pyridine and stylene was changed to 1:3 mol, that is the amounts of 4-vinyl pyridine, stylene, 2,2'-azobisisobutyronitrile and ethanol are 105.14 g 312.45 g (3,000 m mol), 1.34 g (8 m mol) and 726.70 g respectively Table 6 shows the description above in figures.

For the convenience of easy understanding and easy calculation, the amount of 4-vinyl pyridine is uniformly made one mol.

Discs taken from another adsorbent made in the same process of Working Example 1 were filled in another column in the same manner as in Working Example 1, and a suspension with *Escherichia coli* concentration of $2.3 \times 10^8$/ml of 0.85% salt water was sent through the column at a velocity of 70 ml/hr.

Table 7 shows the results of removal rate of living microorganisms in the filtrate, which was taken at regular intervals of time.

WORKING EXAMPLE 7

An absorbent of microorganisms was obtained as described in Working Example 1, except that methyl methacrylate was used instead of stylene and the ratio of 4-vinyl pyridine and stylene was 1:1.5 mol, that is the amounts of methyl methacrylate and ethanol are 150.18 g (1,500 m mol) and 526.37 g respectively.

Table 8 shows the description above in figures.

For the convenience of easy understanding and easy calculation, the amount of 4-vinyl pyridine is uniformly made one mol.

As in Working Example 1, a suspension with *Escherichia coli* concentration of $3.8 \times 10^8$/ml in 0.85% salt water was sent through a column at a velocity of 50 ml/hr, and the rate of removal was taken. Table 7 shows the results.

Table 7 shows that the proportions of 4-vinyl pyridine and vinyl monomer, which are raw material for vinyl copolymers of the present invention, affect adsorption of microorganisms.

Table 7 also shows that even when a component of vinyl monomers is changed, an adsorbent of microorganisms with satisfactory adsorptive efficiency can be obtained.

TABLE 6

| chemical compound | 4-vinyl pyridine | stylene | benzyl bromide | 2,2'-azobisisobutyronitrile | ethyl alcohol |
|---|---|---|---|---|---|
| abbreviation | 4VP | ST | BzBr | AIBN | EtOH |
| ratio of monomer | 1 | 3 | | | |
| mol % (monomer = 100) | 25 | 75 | 25 | 0.2 | |
| molecular weight (g/mol) | 105.14 | 104.15 | 171.04 | 164.21 | 46.07 |
| purity (%) | 100 | 100 | 98 | 98 | 99 |
| calculative annexing (m mol) | 1,000 | 3,000 | 1,000 | 8 | |
| annexing amount (g) | 105.14 | 312.45 | 174.53 | 1.34 | 726.70 |

TABLE 7

| | Working Example 1 | Working Example 6 | Working Example 7 |
|---|---|---|---|
| vinyl monomer | styrene | styrene | methyl methacrylate |

TABLE 7-continued

| | Working Example 1 | Working Example 6 | Working Example 7 |
|---|---|---|---|
| 4-vinyl-pyridine/ vinyl monomer | 40/60 | 25/75 | 40/60 |
| micro-organisms in water (No./ml) | $4.6 \times 10^8$ | $2.3 \times 10^8$ | $3.8 \times 10^8$ |
| micro-organisms in filtrated water 1 hr. later (No./ml) | $1.4 \times 10^4$ | $1.4 \times 10^6$ | $8.0 \times 10^3$ |
| rate of removal (%) | 99.997 | 99.4 | 99.998 |
| micro-organisms in filtrated water 2 hrs. later (No./ml) | $3.7 \times 10^5$ | $6.4 \times 10^6$ | $6.1 \times 10^5$ |
| rate of removal (%) | 99.92 | 97.2 | 99.84 |

TABLE 8

| chemical compound | 4-vinyl pyridine | methyl metha-crylate | benzyl bromide | 2,2'-azobisiso-buty-ronitrile | ethyl alcohol |
|---|---|---|---|---|---|
| abbreviation | 4VP | MMA | BzBr | AIBN | EtOH |
| ratio of monomer | 1 | 1.5 | | | |
| mol % (monomer = 100) | 40 | 60 | 40 | 0.2 | |
| molecular weight (g/mol) | 105.14 | 100.12 | 171.04 | 164.21 | 46.07 |
| purity (%) | 100 | 100 | 98 | 98 | 99 |
| calculative annexing (m mol) | 1,000 | 1,500 | 1,000 | 5 | |
| annexing amount (g) | 105.14 | 150.18 | 174.53 | 0.84 | 526.37 |

WORKING EXAMPLE 8

An adsorbent of microorganisms was obtained in the same process as in Working Example 1, except that a porous base material was made of needlepunch nonwoven fabric of 126 g/m$^2$ and 0.87 mm in thickness, which is made of polyester fiber (1.5 deniers).

Stamping out discs whose diameter was 3 cm from the absorbent, and filling another column, whose inside diameter was 3 cm, with 23 of the discs, a suspension with *Escherichia coli* concentration of $5.5 \times 10^8$/ml in 0.85% salt water was sent through the column at a velocity of 35 ml/hr.

Table 9 shows the results of removal rate of microorganisms in the filtrate, which was taken at regular intervals of time.

WORKING EXAMPLE 9

An adsorbent of microorganism was obtained in the same process as in Working Example 1, except that a porous base material was made of needlepunch nonwoven fabric of 151 g/m$^2$ and 1.11 mm in thickness, which is made of acrylic fiber (1.3 deniers).

Stamping out discs whose diameter was 3 cm from the absorbent, and filling a column whose inside diameter was 3 cm with 18 of the discs, a suspension with *Escherichia coli* concentration of $3.9 \times 10^8$/ml in 0.85% salt water was sent through the column at a velocity of 50 ml/hr.

Table 9 shows the results of removal rate of microorganisms in the filtrate, which was taken at regular intervals of time.

WORKING EXAMPLE 10

An adsorbent of microorganisms was obtained in the same process as in Working Example 1, except that a porous base material was made of wet-type nonwoven fabric of 150 g/m$^2$ and 1.05 mm in thickness, which is made of glass fiber (6 $\mu$m).

Stamping out discs whose diameter was 3 cm from the adsorbent, and filling another column whose inside diameter was 3 cm with 24 of the discs, a suspension with *Escherichia coli* concentration of $2.8 \times 10^8$/ml in 0.85% salt water was sent through the column at a velocity of 55 ml/hr.

Table 9 shows the results of removal rate of microorganisms in the filtrate, which was taken at regular intervals of time.

WORKING EXAMPLE 11

An adsorbent of microorganisms was obtained in the same process as in Working Example, 1 except that a porous base material was made of needlepunch nonwoven fabric of 135 g/m$^2$ and 0.90 mm in thickness, which is made of rayon fiber (1.5 deniers).

Stamping out discs whose diameter was 3 cm from the adsorbent, and filling a column whose inside diameter was 3 cm with 26 of the discs, a suspension with *Escherichia coli* concentration of $3.3 \times 10^8$/ml in 0.85% salt water was sent through the column at a velocity of 55 ml/hr.

Table 9 shows the results of removal rate of microorganisms in the filtrate, which was taken at regular intervals of time.

Table 9 also shows that the type of porous material affects adsorption of an adsorbent of microorganisms a little, but all adsorbents still retain an adsorptive power.

TABLE 9

| | Working Example 8 | Working Example 9 | Working Example 10 | Working Example 11 |
|---|---|---|---|---|
| porous material | NP nonwoven fabric | NP nonwoven fabric | wet-type nonwoven fabric | NP nonwoven fabric |
| made of | polyester | acrylic | glass | rayon |
| micro-organisms in water (No./ml) | $5.5 \times 10^8$ | $3.9 \times 10^8$ | $2.8 \times 10^8$ | $3.3 \times 10^8$ |
| micro-organisms in filtrated water 1 hr. later (No./ml) | $5.5 \times 10^8$ | $7.8 \times 10^4$ | $5.6 \times 10^5$ | $2.3 \times 10^5$ |
| remove rate (%) | 99.0 | 99.98 | 99.8 | 99.93 |
| micro-organisms in filtrated water 2 hrs. later (No./ml) | $2.5 \times 10^7$ | $1.2 \times 10^6$ | $4.2 \times 10^6$ | $2.0 \times 10^6$ |
| removal rate (%) | 95.5 | 99.7 | 98.5 | 99.4 |

WORKING EXAMPLE 12

An adsorptive resin was obtained as described in Working Example 6.

Table 6 shows the contents of the above operation.

A nonwoven fabric (90 g/m$^2$, 0.5 mm in thickness) was obtained by water entangling a fiber web made of rayon fiber (1.5 deniers)

An adsorbent of microorganisms, the proportion of copolymers against the nonwoven fabric of which was 1.5 wt %, was obtained in the steps:

dissolving said adsorptive resin of microorganisms into an ethanol solution;

also impregnating the ethanol solution, in which germicidal zeolite powder (Kanebo's Bactekiller) is scattered the weight ratio of vinyl copolymers and germicidal zeolite powder being 97.3, into said nonwoven fabric; and drying at 75° C.

Said absorbent of microorganisms (5 cm×50 cm) made into a spiral shape was put in a container and a 200 ml suspension of 0.85% sterile salt water in which colon bacilli were suspended ($1\times10^2$/ml) was also put in the container. The suspension was stirred with a magnetic stirrer. Two hours later, the number of live colon bacilli in the liquid was measured by the agar plate culture method, and the measurement 0/ml was obtained, showing the $2\times10^4$ ($1\times10^2$/ml×200 ml) of colon bacilli were adsorbed.

Next, the adsorbent of microorganisms which had adsorbed colon bacilli was taken out, cut into 5 cm×5 cm pieces and were placed on agar culture media, cultured for 48 hours at 32° C. and the number of colonies was counted. These were two colonies of colon bacilli on an agar culture medium.

The result shows that the adsorbent of Working Example 12 is excellent in adsorption of colon bacilli and possesses a function to kill colon bacilli. Therefore, it is apparent that the adsorbent of Working Example 12 is capable of effectively removing microorganisms in water without clogging the system.

WORKING EXAMPLE 13

An adsorptive resin was obtained as described in Working Example 1, except that the ratio of 4-vinyl pyridine and stylene was changed to 1:2.5 mol, that is the amounts of 4-vinyl pyridine, stylene, 2,2'-azobisisobutyronitrile and ethanol are 105.14 g, 260.38 g (2,500 m mol), 1.17 g (7 m mol) and 662.42 g respectively.

Table 10 shows the description above in figures.

An adsorbent of microorganisms (adsorptive resin is 1.5 wt % of nonwoven fabric) was obtained by impregnating an ethanol solution of said adsorptive resin, powdered antibacterial zeolite and lithium chloride in the proportion of 100:3:150 into a nonwoven fabric and drying at 75° C.

Said adsorbent (10 cm×120 cm) was pleated and made into a filter unit of 10 cm×10 cm. A spray box of colon bacilli was installed on the upperstream side of the filter unit and a suction pump with a membranous filter of 0.45 μm was installed on the downstream side.

After having moisturized the adsorbent well by sending through sterile moist air for 30 minutes, a diluted isotonic sodium chloride solution containing colon bacilli was sprayed and an atmosphere containing colon bacilli was sucked by the pump at a speed of 10 l/min. for 2 minutes.

After that operation, the filter unit made of an adsorbent of microorganisms which had adhered colon bacilli was taken out and cut into pieces of 5 cm×5 cm and then put on agar cultural media, cultured for 48 hours at 32° C. There were three colonies of colon bacilli on an agar cultural medium.

The result shows that the adsorbent of Working Example 13 is excellent in adsorptive power of colon bacilli and possesses a germicidal power of adhered colon bacilli. The result also shows that the adsorbent of microorganisms of Working Example 13 does not cause the system to clog and is capable of efficiently removing microorganisms in an atmosphere.

WORKING EXAMPLE 14

An adsorptive resin was obtained as described in Working Example 13.

Table 10 shows the contents of the above operation.

On the other hand, a fiber web made of separate-type fiber (0.3 denier after separation) comprising compositions of polyester and nylon was treated by water entanglement, and a nonwoven fabric of 90 g/m$^2$ and 0.5 mm in thickness was obtained.

An adsorbent of microorganisms (adsorptive resin is 1.5 wt % of nonwoven fabric) was obtained by impregnating an ethanol solution of said adsorptive resin and lithium chloride in the proportion of 100:150 into the nonwoven fabric and drying at 75° C.

Said adsorbent (10 cm×120 cm) was pleated and made into a filter unit of 10 cm×10 cm. A spray box of colon bacilli was installed on the upperstream side of the filter unit and a suction pump with a membranous filter of 0.45 μm was installed on the downstream side.

Removing said filter unit as a blank, a diluted isotonic sodium chloride solution containing solon bacilli was sprayed and an atmosphere containing colon bacilli was sucked by the pump at a speed of 10 l/min for 2 minutes.

After having moisturized the absorbent well by sending through sterile moist air for 5 minutes, a diluted isotonic sodium chloride solution containing colon bacilli was sprayed and an atmosphere containing colon bacilli was sucked by the pump at a speed of 10 l/min. for 2 minutes.

Impregnating a liquid medium into the membranous filter as a blank and the membranous filter after going through said filter unit, the filters were cultured for 24 hours at 32° C. and the number of colonies of colon bacilli was counted each. The removal rates of colon bacilli taken from the counting are shown in Table 11.

TABLE 10

| chemical compound | 4-vinyl pyridine | stylene | benzyl bromide | 2,2'-azobisiso-buty-ronitrile | ethyl alcohol |
|---|---|---|---|---|---|
| abbreviation | 4VP | ST | BzBr | AIBN | EtOH |
| ratio of monomer | 1 | 2.5 | | | |
| mol % (monomer = 100) | 28.57 | 71.43 | 28.57 | 0.2 | |
| molecular weight (g/mol) | 105.14 | 104.15 | 171.04 | 164.21 | 46.07 |
| purity (%) | 100 | 100 | 98 | 98 | 99 |
| calculative annexing (m mol) | 1,000 | 2,500 | 1,000 | 7 | |
| annexing | 105.14 | 260.38 | 174.53 | 1.17 | 662.42 |

TABLE 10-continued

| chemical compound | 4-vinyl pyridine | stylene | benzyl bromide | 2,2'-azobisiso-buty-ronitrile | ethyl alcohol |
|---|---|---|---|---|---|
| amount (g) | | | | | |

TABLE 11

| | Working Example 14 |
|---|---|
| Number of Colonies (blank) | 285 |
| Number of Colonies after going through Adsorbent | 63 |
| Removal Rate (%) | 78 |

As is apparent from Table 11, the adsorbent of microorganisms of Working Example 14 is excellent in adsorptive power and is capable of effectively adsorbing microorganisms in an atmosphere.

The "agar plate culture method" which is used throughout the working examples is approximately as follows.

It is the most popular method to count the number of living microorganisms. However, in case of a lowly contaminated sample, namely less than the range 10 to 30/g(ml), the method is not utilized as the count is not accurate.

(1) Subjects:

Internal solidifier (dispersion solidifier), X-ray contrast medium, local liquid medicine, hydrophile ointment, liquid medicine containing insoluble matter, general internal liquid medicine, other water soluble solidifiers, etc.

(2) Amount:

Generally 1 g (ml), if possible, 10 g (ml).

(3) Medium:

Use either the following (1) or (2).

(1) SCD agar: in case a sample does not contain any antiseptic substances or germicides.

(2) SCDLP agar: in case a sample contains an antiseptic substance or a germicide.

(4) Container:

Petri dishes of 8.5 to 9.0 cm.

(5) Culturing:

The supernatant liquid of an undiluted or diluted solution of a regulated sample is divided into Petri dishes 1 ml each. Usually two or more Petri dishes are used for a single sample. Each dish of the liquid is poured in media (15 to 20 ml each) which have been melted by heat and kept at 48° C. to 50° C., and mixed well by revolving the media. After having them solidified horizontally, the surfaces are dried well avoiding infection with microorganisms. These media are held upside down for at least 72 hours at 30° C. to 32° C. and the number of colonies is counted.

When the concentration of a sample is high, or a sample is already turbid before the culturing, the amount should be 0.5 ml and four or more Petri dishes should be used.

(6) Judgment:

Count the number of colonies in each Petri dish, calculate the average number in each diluted solution in each step, calculate the average in terms of the amount of the sample and the rate of dilution, and get the number of living microorganisms for every gram (ml) of the subject. The counting method of colonies is as follows.

1) In case counting the number of microorganisms after 72 hours of culturing is not possible due to the generation of proliferation of colonies, use the number of microorganisms taken after 48 hours instead.

b 2) In principle, use the number of microorganisms taken for a sample at a stage when the number of colonies in each Petri dish is in the range 20 to 200 (30 to 300 is also acceptable) or in the vicinity.

3 ) When the number of colonies in each Petri dish is less than 10 at any stage of the dilution, count the number of colonies of the least diluted one, and do not record the average of the actual numbers. For instance, record as $<1.0\times10^2$ in the case of a diluted liquid to ten times. It is useful to keep the records of colors, shapes, sizes, etc. of the generated colonies to later determine the types of microorganisms.

A adsorptive resin as described above possesses an excellent adsorptive power and is soluble in an organic solvent. Therefore, it can be impregnated into other base materials as a solution or can be coated. Also the use of the adsorptive resin is not limited as in the case of cross-linked polyvinyl pyridinium halide which can be treated only as a solid matter. The surface area per unit weight of said adsorptive resin of microorganisms, which is an absolutely important factor for an effective adsorbent, can be freely obtained by selecting base materials and a desired adsorbent of microorganism can be also obtained. Adsorptive resins of the present invention are insoluble in water and therefore do not contaminate the environment.

The adsorbent of microorganism, of the present invention when used in water treatment, effectively adsorbs microorganisms and the adsorptive power does not deteriorate with time, hardly causing clogging of the system. When the adsorbent is used for a biosensor or a bioreactor, it can efficiently collect organisms in the air or water in a living and active state. Especially when a three-dimensional base material such as a nonwoven fabric is used, the surface area to contact with reactive substances as well as solutions to be analyzed becomes large, enabling organic catalytic functions to function satisfactorily.

Therefore, the adsorbent of microorganisms is very suitable for a bioreactor or a biosensor that utilizes enzyme contained in microorganisms, produces reactive products and sorts substances.

The adsorbent of microorganisms of the present invention can effectively remove microorganisms by sterilizing, with a germicide, microorganisms collected by an adsorptive resin or by preventing the microorganisms from propagating. Especially when a porous material is used as a base material, an excellent adsorptive power can be expected, for the contact area of the base material is big and the porous material itself gives a filtering effect. The collected microorganisms are either sterilized by a germicide or prevented from propagating. Therefore, the clogging hazard of the system is prevented and the life of the system is elongated.

As described, the adsorbent of microorganisms of the present invention can effectively remove microorganisms in the air or water and it is suitable for a water treatment substance or for a mask or an airfilter.

The adsorbent of microorganisms of the present invention does not contaminate the environments since the germicide is insoluble in water.

The adsorbent of microorganisms of the present invention can collect microorganisms effectively even in the air as it can retain an adsorptive power helped by a moistener. When a porous material is used as a base material, the surface area becomes large, enabling the adsorbent to possess a high adsorptive power of microorganisms, and troubles such as clogging can be effectively prevented.

The adsorbent of microorganisms can collect microorganisms in the air effectively and is suitable for a carrier of a biosensor or a bioreactor.

The adsorbent of microorganisms of the present invention prevents microorganisms collected by the adsorbent from propagating, eliminating trouble such as clogging, and elongates the life of a mask or an airfilter.

Therefore the adsorbent of microorganisms is suitable for a mask or an airfilter.

In accordance with the method of the present invention for making adsorbents of microorganisms, excellent adsorbents of microorganisms can be easily made as the adsorptive resins of the present invention are soluble in an organic solvent, enabling impregnation, spraying and coating of the resins to the surface of a base material.

What is claimed is:

1. A resin for adsorbing microorganisms comprising a vinyl copolymer of the following formula

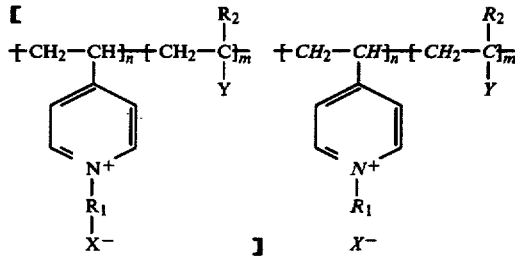

wherein, $R_1$ is a benzyl group, an alkyl group of 4 to 16 carbon atoms or a pentafluorophenylmethyl group, $R_2$ is a hydrogen atom or an alkyl group of 1 to 3 carbon atoms, X is a halogen atom, and Y is a hydrogen atom, an alkyl group of 1 to 3 carbon atoms, a benzyl group, an ether group, a carboxyl group, a carboxylic acid ester group or an aryl group, said vinyl copolymer being insoluble in water and soluble in organic solvent.

2. An adsorbent for microorganisms comprising a vinyl copolymer of the following formula and existing on the surface of a substrate,

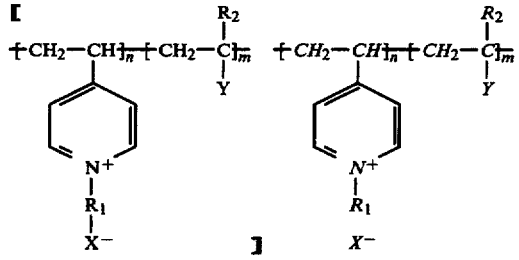

wherein, $R_1$ is a benzyl group, an alkyl group of 4 to 16 carbon atoms or a pentafluorophenylmethyl group, $R_2$ is a hydrogen atom or an alkyl group of 1 to 3 carbon atoms, X is a halogen atom, and Y is a hydrogen atom, an alkyl group of 1 to 3 carbon atoms, a benzyl group, an ether group, a carboxyl group, a carboxylic acid ester group or an aryl group, said vinyl copolymer being insoluble in water and soluble in organic solvent.

3. The adsorbent according to claim 2, wherein said substrate is a porous material.

4. The adsorbent according to claim 3, wherein said substrate is a non-woven fabric.

5. The adsorbent according to claim 2, wherein said vinyl copolymer is existing on the surface of a substrate with a germicidal agent.

6. The adsorbent according to claim 3, wherein said vinyl copolymer is existing on the surface of a substrate with a germicidal agent.

7. The adsorbent according to claim 4, wherein said vinyl copolymer is existing on the surface of a substrate with a germicidal agent.

8. The adsorbent according to claim 5, wherein said germicidal agent is water insoluble.

9. The adsorbent according to claim 6, wherein said germicidal agent is water insoluble.

10. The adsorbent according to claim 7, wherein said germicidal agent is water insoluble.

11. The adsorbent according to claim 2 wherein said vinyl copolymer is existing on the surface of a substrate with a moisture adsorbent.

12. The adsorbent according to claim 3 wherein said vinyl copolymer is existing on the surface of a substrate with a moisture absorbent.

13. The adsorbent according to claim 4 wherein said vinyl copolymer is existing on the surface of a substrate with a moisture absorbent.

* * * * *

UNITED STATES PATENT AND TRADEMARK OFFICE

CERTIFICATE OF CORRECTION

PATENT NO. : Re: 34,740

DATED : September 27, 1994

INVENTOR(S) : Kawabata et al

It is certified that error appears in the above-indentified patent and that said Letters Patent is hereby corrected as shown below:

Title Page, Item [73]: Delete the "k" in "Vilkene";

Column 8, Line 13: After "TABLE" delete "1" and insert --2--;

Column 13, Line 20: Delete "absorbent" and insert --adsorbent--;

Column 13, Line 28: Insert --that-- after "showing";

Column 13, Line 34: Delete "These" and insert --There--;

UNITED STATES PATENT AND TRADEMARK OFFICE

CERTIFICATE OF CORRECTION

PATENT NO. : Re: 34,740

DATED : September 27, 1994

INVENTOR(S) : Kawabata et al

It is certified that error appears in the above-indentified patent and that said Letters Patent is hereby corrected as shown below:

Column 13, line 51: After "figures." insert the following paragraph:

--On the other hand, a fiber web made of separate-type fiber (0.3 denier after separation) comprising compositions of polyester and nylon was treated by water entanglement, and a nonwoven fabric of 100 g/m$^2$ and 0.6 mm in thickness was obtained.--

Column 14, Line 35: Delete "solon" and insert --colon--; and

Column 16, Line 7: Delete "b".

Signed and Sealed this

Twenty-ninth Day of August, 1995

*Attest:*

Bruce Lehman

BRUCE LEHMAN

*Attesting Officer*

*Commissioner of Patents and Trademarks*